United States Patent [19]

Kurose

[11] 4,370,500

[45] Jan. 25, 1983

[54] COMPOUND: D-N-(2-AMINO-2-PHENETHYL)-2-METHOXYETHYLAMINE AND PROCESS FOR PREPARING THE SAME BY SELECTIVE CRYSTALLIZATION

[75] Inventor: Nancy S. Kurose, Norwalk, Conn.

[73] Assignee: American Cyanamid Company, Stamford, Conn.

[21] Appl. No.: 958,216

[22] Filed: Nov. 6, 1978

[51] Int. Cl.³ .............................................. C07C 87/28
[52] U.S. Cl. ............................ 564/304; 260/501.17; 564/372
[58] Field of Search ................ 260/570.5 PA, 501.17; 564/304, 372

[56] References Cited

U.S. PATENT DOCUMENTS

| | | | |
|---|---|---|---|
| 3,312,733 | 4/1967 | Howe | 260/501.18 |
| 3,478,101 | 11/1969 | Tsuruga et al. | 260/570.6 |
| 3,819,689 | 6/1974 | Thompson et al. | 260/570.6 X |
| 3,845,070 | 10/1974 | McMenim et al. | 260/570.5 X |
| 3,847,991 | 11/1974 | Bernardi et al. | 260/570.5 X |
| 3,865,836 | 2/1975 | Van Gelder et al. | 260/570.5 X |
| 3,887,617 | 6/1975 | Seebach et al. | 260/570.5 X |

Primary Examiner—Robert V. Hines
Attorney, Agent, or Firm—Gordon L. Hart

[57] ABSTRACT

There is provided a new compound: d-N-(2-amino-2-phenethyl-2-methoxyethylamine useful in the direct synthesis of levamisole. The compound is prepared by slurrying the racemic N-(2-amino-2-phenethyl)-2-methoxyethylamine with dibenzoyl-d-tartaric acid as the resolving agent in an aqueous acidic menstruum containing ammonium chloride, heating the resultant mixture, preferably under reflux, cooling and filtering the resultant mixture to recover crystals rich in the desired d-amine compound, hereinabove noted.

5 Claims, No Drawings

COMPOUND: D-N-(2-AMINO-2-PHENETHYL)-2-METHOXYETHYLAMINE AND PROCESS FOR PREPARING THE SAME BY SELECTIVE CRYSTALLIZATION

The present invention relates to the resolution of dl-N-(2-amino-2-phenethyl)-2-methoxyethylamine. More particularly, it relates to the resolution of dl-N-(2-amino-2-phenethyl)-2-methoxyethylamine by utilizing a resolving agent, namely, dibenzoyl-d-tartaric acid whereby the d-isomer is obtained. Still more particularly, the invention is concerned with the resolution of dl-N-(2-amino-2-phenethyl)-2-methoxyethylamine by utilizing dibenzoyl-d-tartaric acid in an aqueous acidic menstruum containing ammonium chloride whereby racemic mixtures enriched in the d-isomer is obtained by recovering resultant crystals.

In a copending application of Sivaraman Raghu filed concurrently herewith, Ser. No. 958,222 and now abandoned there is disclosed a process for the preparation of tetramisole in which there is employed the intermediate: dl-N-(2-amino-2-phenethyl)-2-methoxyethylamine. This intermediate is prepared from the reaction of styrene oxide and 2-methoxyethylamine to obtain dl-N-(2-hydroxy-2-phenethyl)-2-methoxyethylamine which in turn is reacted with acidified acetonitrile to prepare dl-N-(2-acetamido-2-phenethyl)-2-methoxyethylamine which is then hydrolyzed to dl-N-(2-amino-2-phenethyl)-2-methoxyethylamine. The latter principal intermediate is next ring-closed with carbon disulfide and acid to prepare tetramisole which is then conventionally resolved with p-toluenesulfonyl-L-glutamic acid to prepare desired levamisole of relatively low overall yield. If a process could be provided to prepare levamisole without the conventional step of resolving tetramisole, a long felt need in the art would be realized.

To this end, it has been unexpectedly found that the aforementioned principal intermediate, namely, dl-N-(2-amino-2-phenethyl)-2-methoxyethylamine, can be directly resolved to obtain the d-isomer in good yield and optical purity. With the obtainment of this isomer, levamisole in yields and purity hitherto unattained can be directly synthesized utilizing carbon disulfide ring closure followed by acidification.

According to the process of the invention, the racimate: dl-N-(2-amino-2-phenethyl)-2-methoxyethylamine is treated with dibenzoyl-d-tartaric acid as the resolving agent. There is formed a slurried solution with acidified water and ammonium chloride, all being present in certain well-defined amounts. There is then obtained the desired isomer having an optical rotation ranging from +28° to +31° (c=1 in $CHCl_3$).

There is initially established a mol ratio of the dl-N-(2-amino-2-phenethyl)-2-methoxyethylamine, dibenzoyl-d-tartaric acid, and hydrochloric acid ranging from 1:1–1.1:1–0.9, respectively, in an aqueous menstruum and in the presence of from about 1 to about 15 mols of ammonium chloride sufficient to maintain an aqueous slurry, the amount of water ranging from about 100 to about 500 mols. The resultant slurry is subjected to heating usually under reflux conditions, for from one-half to five hours, and preferably from one to three hours, cooling and filtering the resultant mixture, and recovering crystals of desired salt which is then decomposed to obtain desired d-amine of good optical purity and yield. If desired, the recovered crystals prior to decomposition to the desired d-amine can be reheated in the presence of ammonium chloride as in the first treatment stage, and then recovered to ensure a good crop of desired crystals.

Decomposition of the aforementioned salt to recover d-amine may be effected by conventional techniques. One such is subjecting the filtered salt complex to the action of a suitable alkali, such as ammonium hydroxide, sodium hydroxide or potassium hydroxide and then extracting the desired amine with a selective solvent therefor such as methylene chloride, which mixture is next subjected to evaporation and dried to recover good yield of the desired d-isomer.

The following non-limiting examples are incorporated herein to further illustrate the present invention. Unless otherwise specified, the parts given are by weight.

EXAMPLE 1

A slurried solution of 1.94 parts of dl-N-(2-amino-2-phenethyl)-2-methoxyethylamine and 1.60 parts of ammonium chloride in 20 parts of water is admixed with 0.9 parts (by volume) of concentrated hydrochloric acid and 4.14 parts of dibenzoyl-d-tartaric acid monohydrate and refluxed with vigorous stirring for one hour. The mixture is then cooled to room temperature and allowed to stand for three hours. It is then filtered, and washed with 10 parts of water. Resultant filter cake is next resuspended in 20 parts of water, treated with 1.60 parts of ammonium chloride and 0.1 part (by volume) of concentrated hydrochloric acid, and, refluxed for one hour. Resultant mixture is allowed to cool at room temperature and the mixture is next filtered and washed with water.

The resultant filter cake is then suspended in water, made alkaline with 10% sodium hydroxide and extracted with methylene chloride. Resultant extracts are combined, dried and evaporated to dryness to give 0.88 part of (45.4% of starting dl) of d-N-(2-amino-2-phenethyl)-2-methoxyethylamine, $\alpha_D^{20} = +29.6°$ (C=1, $CHCl_3$).

EXAMPLE 2

A slurried solution of 1.94 parts of dl-N-(2-amino-2-phenethyl)-2-methoxyethylamine and 6.42 parts of ammonium chloride in 40 parts of water is treated with 1.0 part (by volume) of concentrated hydrochloric acid and 3.76 parts of dibenzoyl-d-tartaric acid monohydrate and refluxed with vigorous stirring for two hours. The mixture is then chilled in an ice-water bath for ½ hour and filtered. Decomposition of the salt cake as in Example 1 above yields 0.62 part of d-N-(2-amino-2-phenethyl)-2-methoxyethylamine having $\alpha_D^{20} = +29.4°$ (c=1, $CHCl_3$).

I claim:

1. The compound: d-N-(2-amino-2-phenethyl)-2-methoxyethylamine.

2. A process for the recovery of the compound of claim 1, d-N-(2-amino-2-phenethyl)-2-methoxyethylamine, which comprises the steps of: forming a slurried solution of a mixture of dl-N-(2-amino-2-phenethyl)-2-methoxyethylamine, and dibenzoyl-d-tartaric acid in an aqueous acidic menstruum containing ammonium chloride, refluxing the resultant slurried solution, cooling the latter, filtering and decomposing the latter to obtain the desired d-N-(2-amino-2-phenethyl)-2-methoxyethylamine enantiomer in good optical purity and yield.

3. The process according to claim 2 wherein a first crop of salt crystals is subjected to additional ammonium chloride solution and refluxed prior to recovering the desired d-amine enantiomer.

4. The process according to claim 2 wherein the slurried mixture comprises a mol ratio of 1:1–1.1:1–0.9 of dl-N-(2-amino-2-phenethyl)-2-methoxyethylamine, dibenzoyl-d-tartaric acid and hydrochloric acid, respectively.

5. A process according to claim 4 wherein 1 to 15 mols of ammonium chloride is present and from about 100 to 500 mols of water are added.